United States Patent [19]
Varn

[11] Patent Number: 5,637,078
[45] Date of Patent: Jun. 10, 1997

[54] RESTING HAND ORTHOSIS

[75] Inventor: Harold T. Varn, Lawrenceville, Ga.

[73] Assignee: Restorative Care of America Incorporated, Clearwater, Fla.

[21] Appl. No.: 438,526

[22] Filed: May 10, 1995

[51] Int. Cl.$^6$ .................................................. A61F 5/00
[52] U.S. Cl. .................. 602/21; 602/6; 128/878; 128/879
[58] Field of Search ................ 602/5–8, 20, 21; 128/846, 877, 878–879

[56] References Cited

U.S. PATENT DOCUMENTS

| | | | |
|---|---|---|---|
| 3,295,518 | 1/1967 | Hazlewood et al. | 128/877 |
| 3,526,006 | 9/1970 | Beardmore | 602/21 X |
| 3,703,894 | 11/1972 | Galloway et al. | 602/21 |
| 3,722,508 | 3/1973 | Roberts | 128/877 |
| 3,724,456 | 4/1973 | Waxman | 128/877 |
| 4,798,199 | 1/1989 | Hubbard et al. | 602/21 |
| 4,840,168 | 6/1989 | Lonardo . | |
| 4,862,904 | 9/1989 | West et al. | 128/877 |
| 4,928,712 | 5/1990 | Mele | 128/878 X |
| 4,945,925 | 8/1990 | Garcia | 128/877 |
| 5,121,743 | 6/1992 | Bishop | 128/879 X |
| 5,205,812 | 4/1993 | Wasserman | 128/878 X |

Primary Examiner—Linda C. Dvorak
Attorney, Agent, or Firm—Zarley, McKee, Thomte, Voorhees & Sease

[57] ABSTRACT

The resting hand orthosis of this invention has a substantially rigid splint member which has an inner wrist portion adapted to fit on and receive the inner wrist portion of a patient. The splint also includes an arcuate palm portion extending from the wrist portion to receive the cupped hand of a patient who has their fingers juxtapositioned with the thumb in space gripping position opposite the patient's index finger. The resting hand orthosis of this invention has a substantially rigid splint member which has an inner wrist portion adapted to fit on and receive the inner wrist portion of a patient. The splint also includes an arcuate palm portion extending from the wrist portion to receive the cupped hand of a patient who has their fingers juxtapositioned with the thumb in space gripping position opposite the patient's index finger.

8 Claims, 6 Drawing Sheets

RESTING HAND ORTHOSIS

BACKGROUND OF THE INVENTION

Hand and wrist orthoses exist in the market today and are adapted to support the wrist, hands, and fingers of a patient to accomplish a plurality of corrective functions. However, such devices are often difficult to place on the patient's hand, or to be removed therefrom. They are not normally adaptable to accommodate a resting position of the hand. The liners for such devices are often difficult to assemble and disassemble, and are sometimes not easily cleaned.

It is therefore a principal object of this invention to provide a resting hand orthosis which offers a resting hand position following injury or post surgery conditions.

A further object of this invention is to provide a hand orthosis which will provide support for unstable wrists and which can be used for treatment of wrist and finger contractures.

A still further object of this invention is to provide a hand orthosis which fully extends the joints and supporting arches of the hands to enhance increased mobility and to monitor functional alignment.

A still further object of this invention is to prevent hyperextension of the wrist in the spastic patient, and to prevent inadvertent removal of the orthosis.

A still further object of the invention is to provide a hand orthosis having a liner that is not affixed to the supporting splint by structural features of the splint itself.

These and other objects will be apparent to those skilled in the art.

SUMMARY OF THE INVENTION

The resting hand orthosis of this invention has a substantially rigid splint member which has an inner wrist portion adapted to fit on and receive the inner wrist portion of a patient. The splint also includes an arcuate palm portion extending from the wrist portion to receive the cupped hand of a patient who has their fingers juxtapositioned with the thumb in space gripping position opposite the patient's index finger.

The resting hand orthosis of this invention has a substantially rigid splint member which has an inner wrist portion adapted to fit on and receive the inner wrist portion of a patient.

The splint also includes an arcuate palm portion extending from the wrist portion to receive the cupped hand of a patient who has their fingers juxtapositioned with the thumb in space gripping position opposite the patient's index finger.

DESCRIPTION OF THE PREFERRED EMBODIMENT

Figure 3:
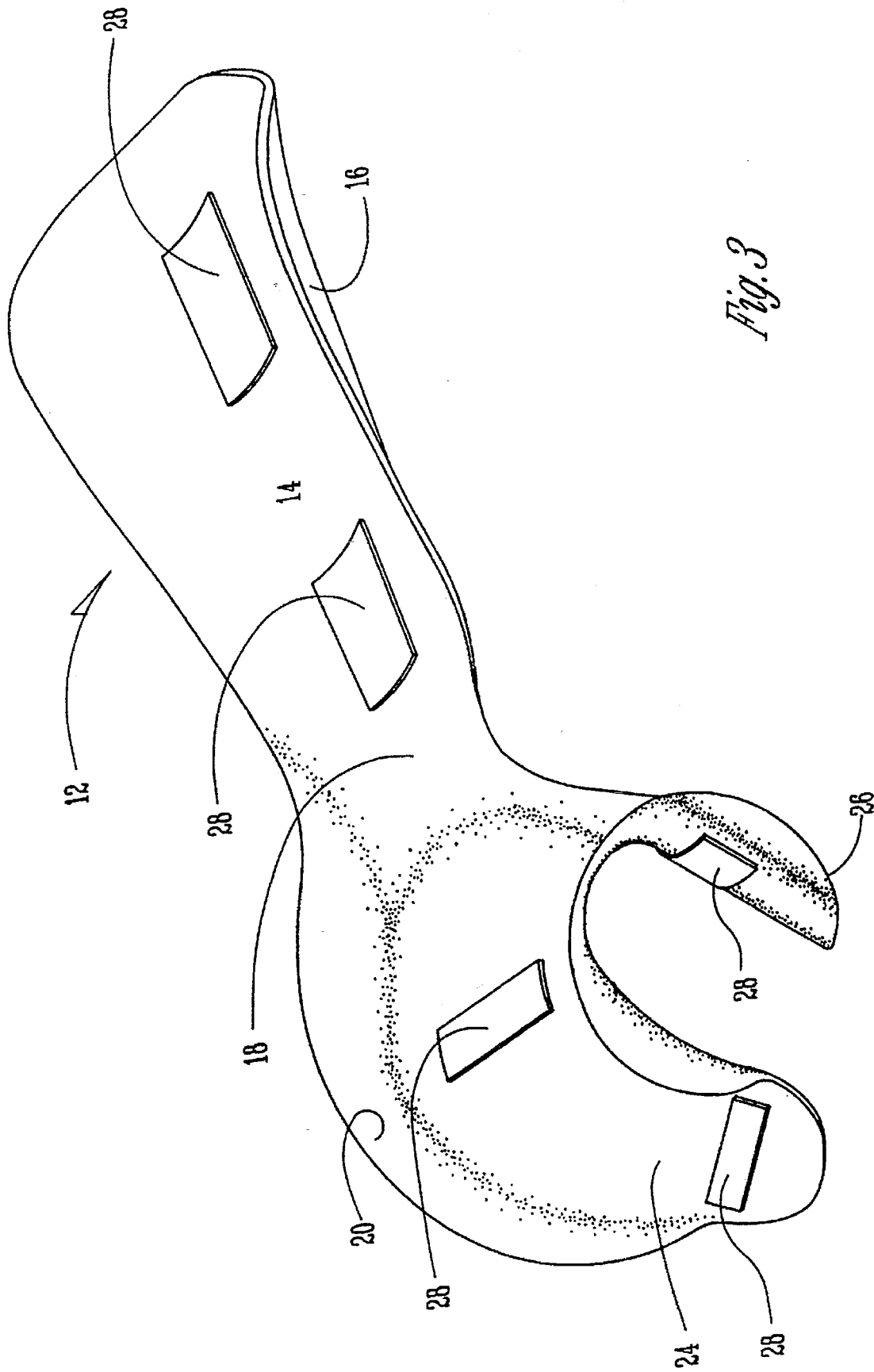
FIG. 3 is a view similar to FIG. 1 but has the liner and attachment straps removed therefrom.
Figure 4:
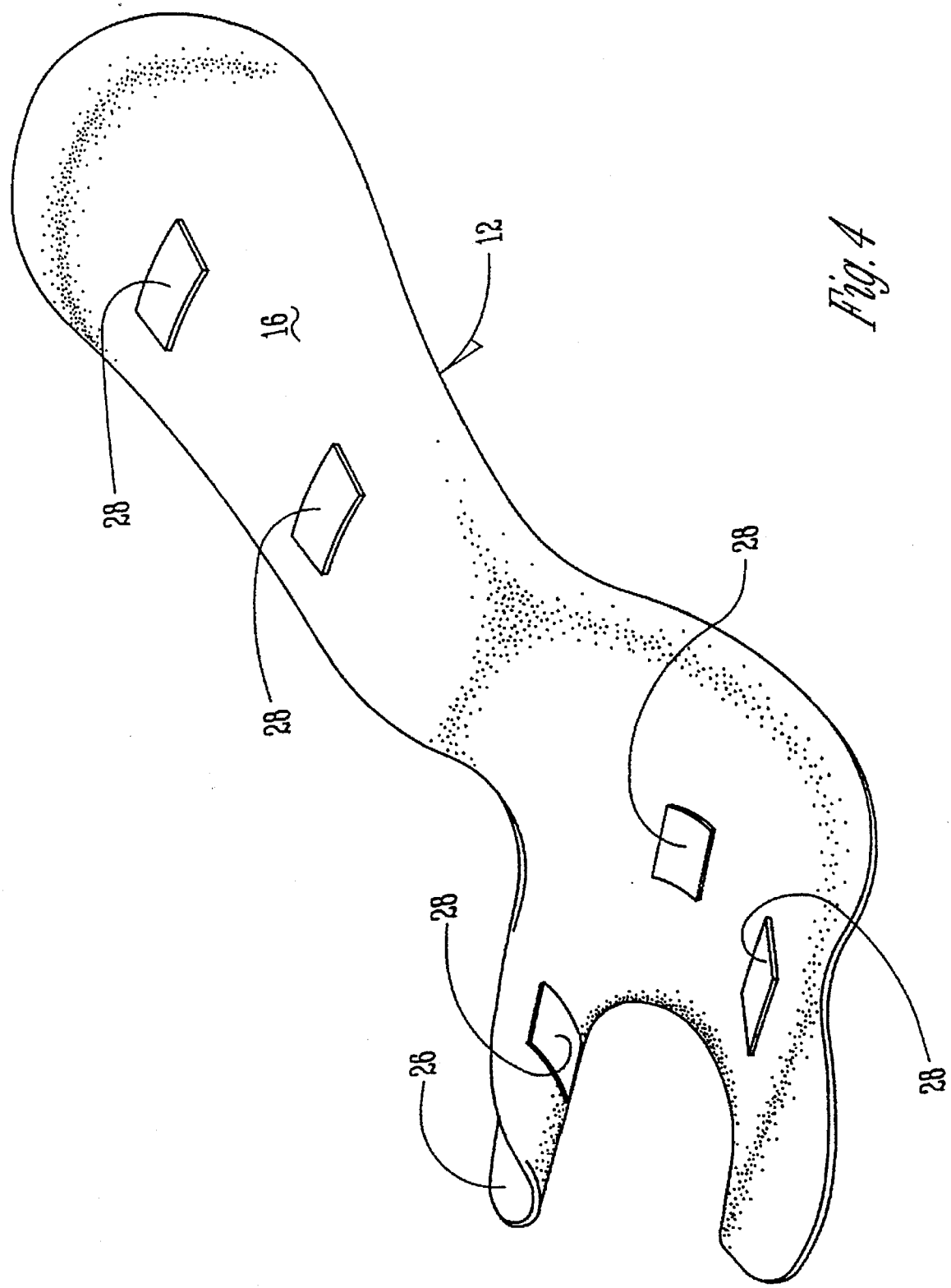
FIG. 4 is a view similar to that of FIG. 2 but shows the liner and straps removed from the splint.

The hand orthosis 10 has a substantially stiff plastic splint 12 best shown in FIGS. 3 and 4. Splint 12 has a inner surface 14, and an outer surface 16. With reference to FIG. 3, the splint 12 includes a wrist portion 18, a hand portion 20, a palm portion 22, a finger portion 24, and a thumb portion 26. For purposes herein, the wrist portion 18 is deemed to include what also might be called a forearm portion.

As will be described hereafter, a plurality of Velcro® fasteners are used in this invention which include hook patches which can be detachably connected to material having a plurality of loops. A plurality of hook patches 28 are permanently secured to splint 12 on both the inner and outer surfaces thereof to secure a flexible, resilient, one-piece liner 30 in position on the inner surface 14 of the splint 12.

Liner 30 has an inner side 32 and a outer side 33. Liner 30 has a wrist portion 18A, a hand portion 20A, a palm portion 22A, a finger portion 24A and a thumb portion 26A which correspond to the portions 18–26, respectively, on splint 12.

Figure 5:
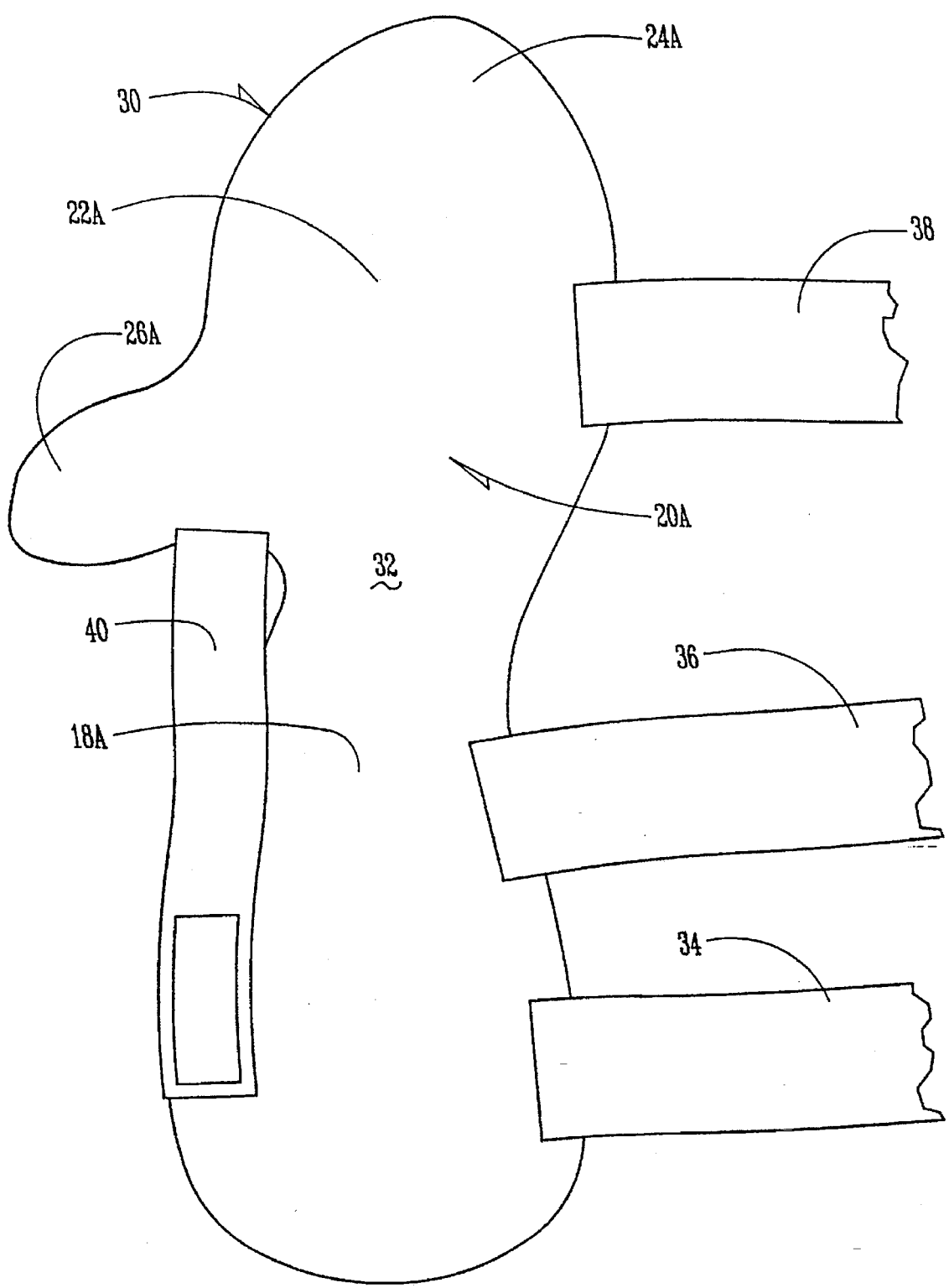
FIG. 5 is a plan view of the detached liner.
Figure 6:
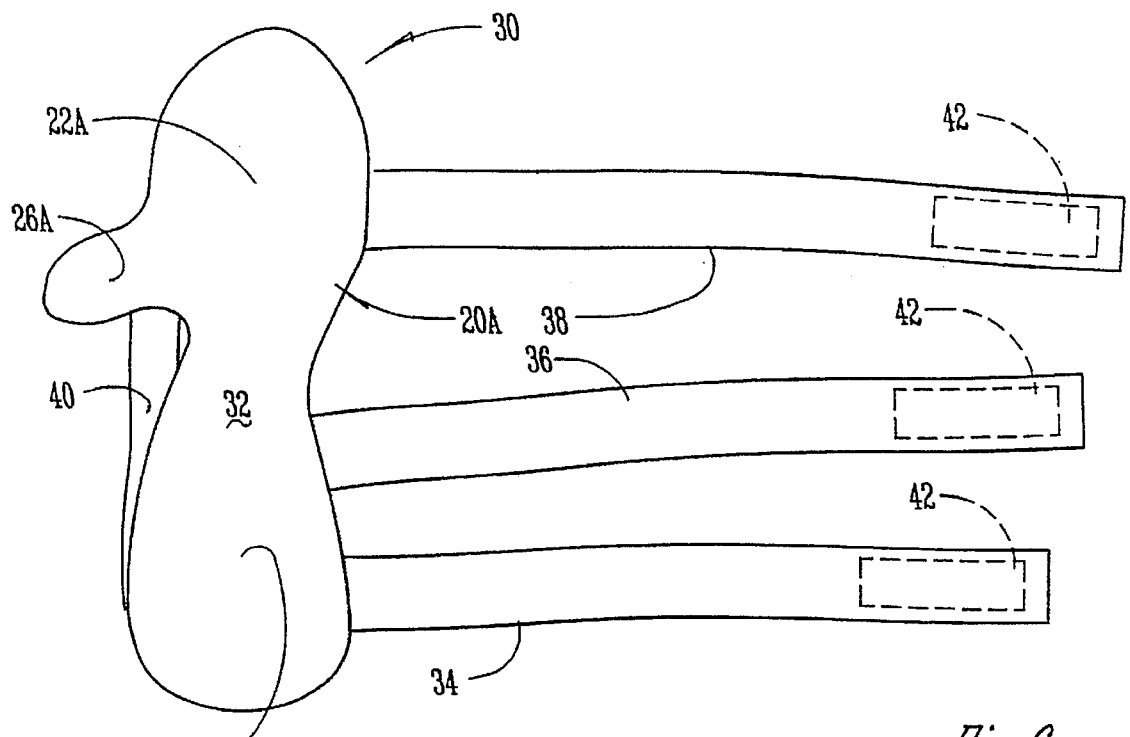
FIG. 6 is a view similar to that of FIG. 5 but is shown at a smaller scale and shows the side of the liner opposite to that shown in FIG. 5.

With reference to FIG. 5, elongated wrist straps 34 and 36 are secured by one of their ends to one edge of liner 30. Similarly, finger strap 38 is secured by one of its ends to the same edge of liner 30. Thumb strap 40 is secured by one of its ends to the liner 30 adjacent the thumb portion 26A. Each of the straps is comprised of loop material which is adapted to be detachably secured to the hook patches 42 which are secured to the other ends of straps 34–40 (FIG. 6).

Figure 7:
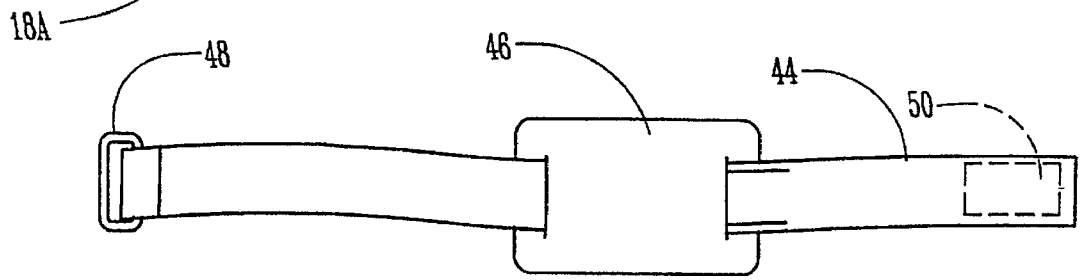
FIG. 7 is a plan view of an auxiliary strap which extends across the palm and in back of the hand to further secure the device to a patient's hand.

An auxiliary palm strap 44 (FIG. 7), is separate from both the liner 30 and the splint 12 and can be used in certain applications for special patient needs. The strap 44 extends through pad 46 and has a buckle fastener 48 on one end thereof. A hook patch 50 is located on the end of strap 44 opposite buckle 48 as shown by the dotted lines in FIG. 7.

Liner 30 is comprised of a foam material which along with the material of the straps described heretofore absorbs perspiration away from the patient's skin, thus promoting good skin integrity.

Figure 8:
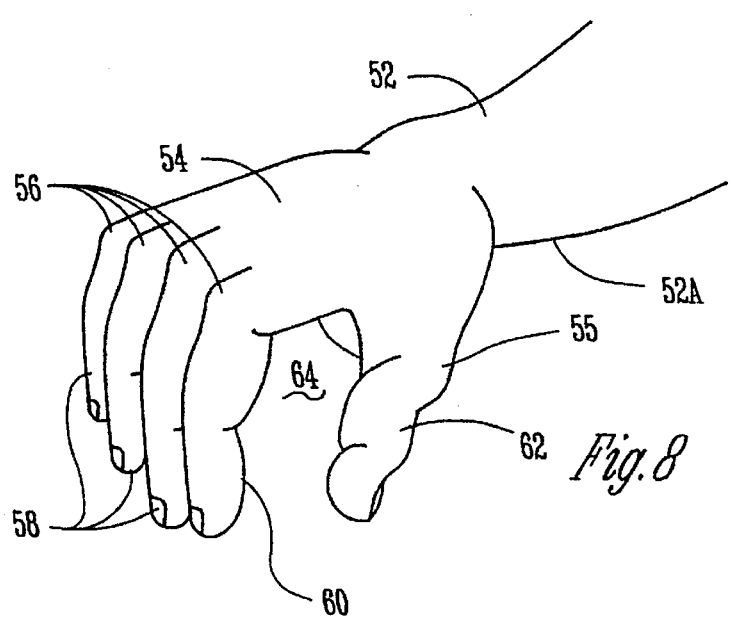
FIG. 8 shows a patient's hand in the general position that it is held by the device of this invention and specifically shows the hand as it would be superimposed over FIG. 1 if the hand were placed in the device of this invention.

With reference to FIG. 8, a patient's forearm, wrist and hand are depicted. The numerals 52 and 52A designate the patient's wrist and inner wrist, respectively; the numeral 54 designates the patient's hand; the numeral 55 designates the patient's palm; the numeral 56 designates the patient's knuckles; the numeral 58 designates three of the patient's fingers, with the numeral 60 designating the index finger; and the numeral 62 designates the patient's thumb. The numeral 64 designates the space between the thumb 62 and the index finger 60 when the hand 54 is in the cupped position shown in FIG. 8.

In operation, the patient's hand 54 is placed in the general position shown in FIG. 8 and inserted onto the hand orthosis so that the inner wrist 52A (FIG. 8) engages the wrist portion of liner 30; the palm 55 (FIG. 8) of the patient engages the portion 22A of the liner 30; and the fingers 58 and 60 of the patient engage the finger portion 24A of the liner 30. Similarly, the thumb 62 engages the thumb portion 26A of the liner.

Figure 1:
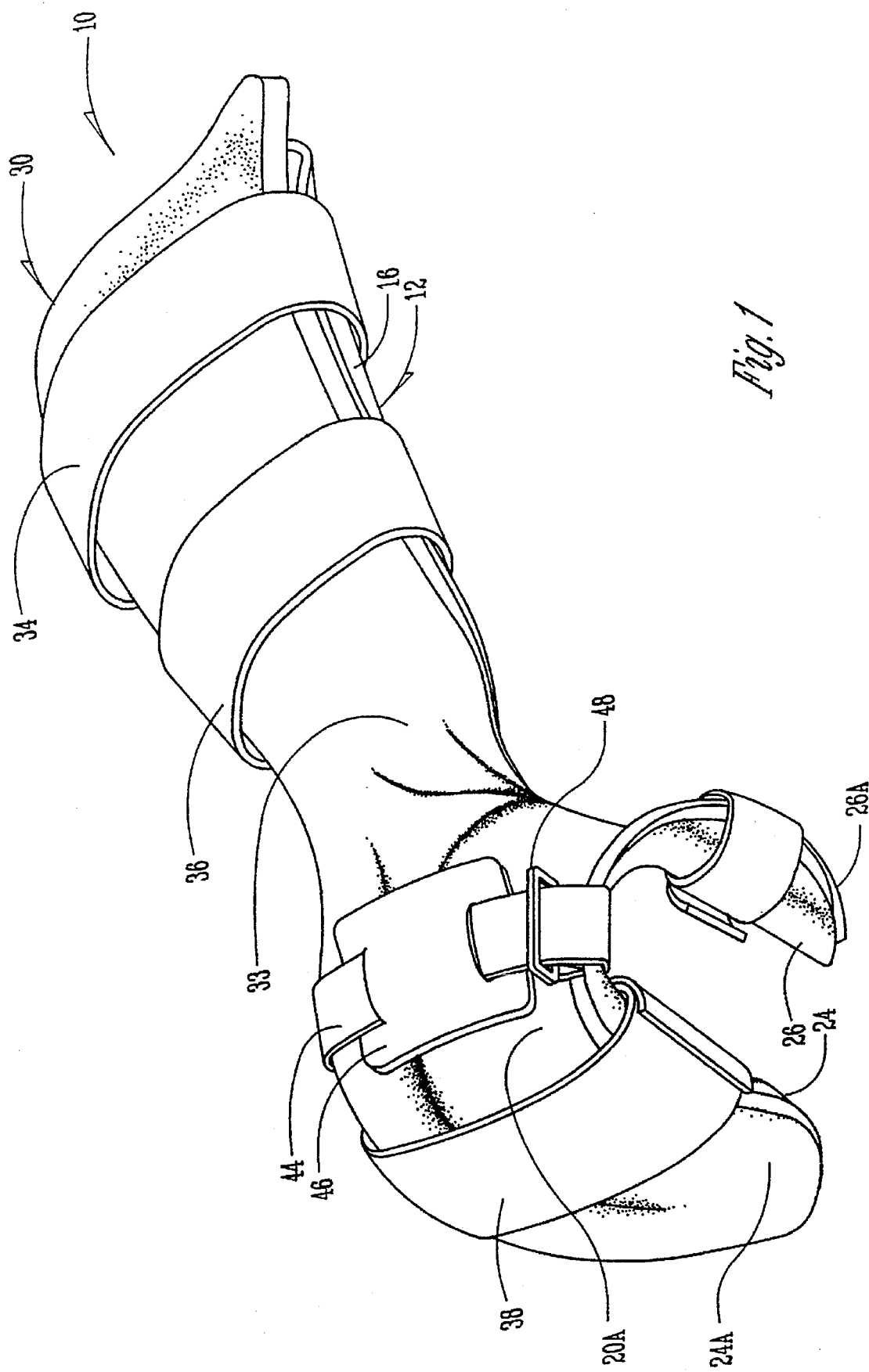
FIG. 1 is a perspective view of the resting hand orthosis of this invention showing primarily the upper surface thereof.
Figure 2:
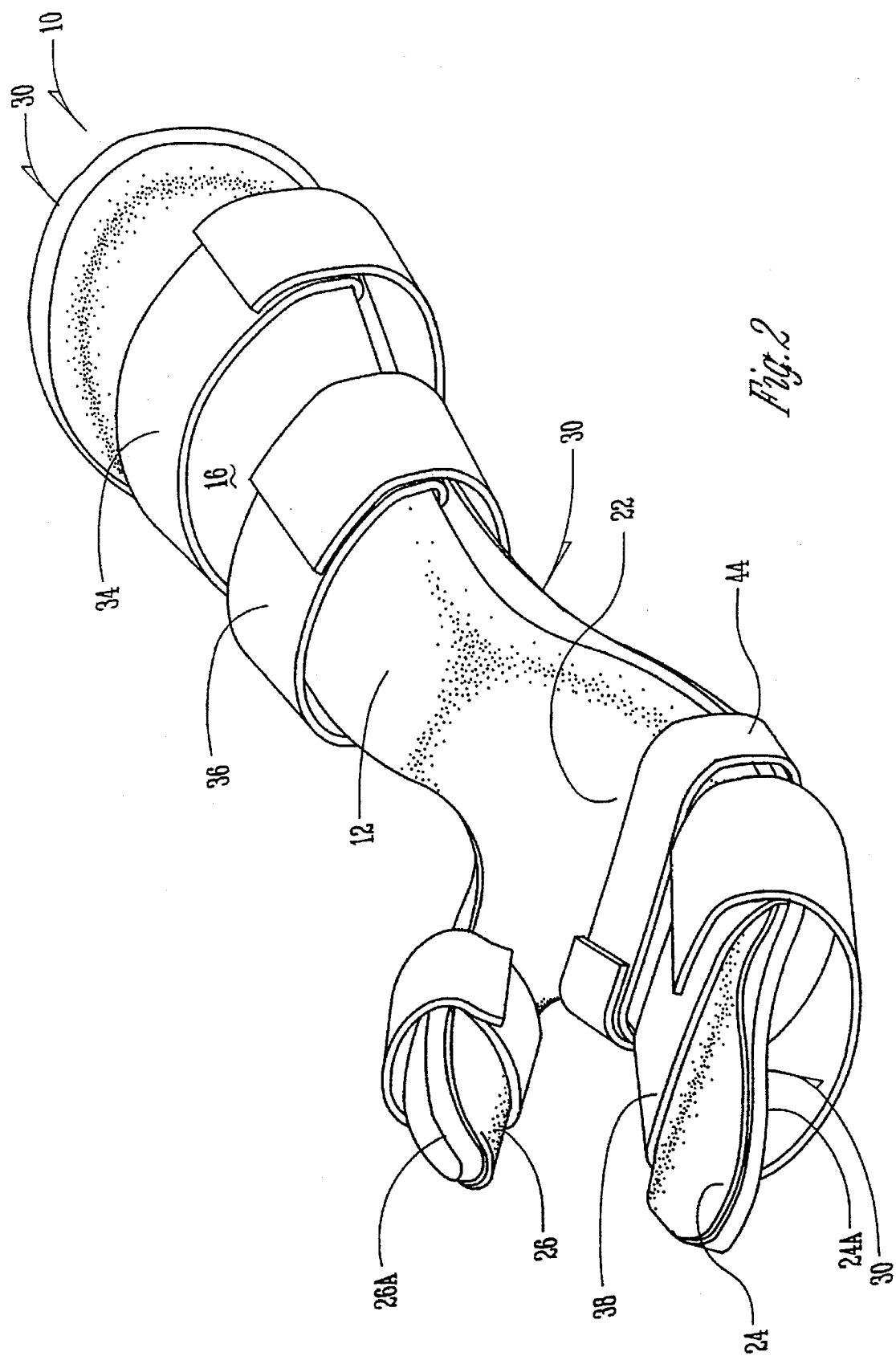
FIG. 2 is a perspective view of the resting hand orthosis of this invention showing primarily the lower surface thereof.

The wrist straps 34 and 36 can then be extended around the wrist and forearm of the patient and secured upon themselves as best shown in FIGS. 1 and 2. Similarly, the finger strap 38 can be extended around the fingers of the patient and secured upon itself as best shown in FIGS. 1 and 2. Lastly, the thumb strap 40 can be extended around the thumb and secured upon itself as best shown in FIGS. 1 and 2.

In the event that the patient has a spastic condition, the strap 44 can be extended around the palm and knuckles of the patient as best shown in FIGS. 1 and 2. This will serve to prevent hyper-extension of the wrist for such a patient, or inadvertent removal of the device.

When it is desired to change the liner 30, the entire liner can be detached from the splint 12 by unfastening the straps 34, 36, 38 and 40 in conventional manner to place the liner in the condition shown in FIG. 5. Thus, the liner can easily be removed in one piece without having, for example, to unthread straps through holes or slots in the splint which is typical of the prior art.

It is therefore seen that this device will achieve all of its stated objectives.

What is claimed is:

1. A resting hand orthosis, comprising,
   a substantially rigid splint member having an inner wrist portion adapted to fit on and receive the inner wrist of a patient;
   an arcuate palm portion extending from said wrist portion and adapted receive a cupped hand of a patient with the fingers juxtapositioned and the thumb in special gripping position opposite the patient's index finger,
   a thumb portion extending downwardly from said palm portion and adapted to receive the inner portion of the thumb,
   a finger portion spaced forwardly from and longitudinally opposite said thumb portion to receive the juxtapositioned fingers of the patient,
   said thumb portion and said finger portion defining therebetween a generally C-shaped void,
   said splint having first and second surfaces said first surface adapted to extend over the inner wrist, palm, and inner surfaces of the thumb and fingers of the patient,
   a resilient liner covering the first surface of said splint,
   and separate strap elements on said liner adapted to extend around the outer surface of the patient's wrist, thumb and fingers and over the second surface of said splint to attach the orthosis to the patient.

2. The device of claim 1 wherein said splint is of one-piece construction.

3. The device of claim 1 wherein said liner is of one-piece construction.

4. The device of claim 1 wherein said splint and said liner are of one-piece construction.

5. The device of claim 1 wherein one of the separate strap elements is mountable on said orthosis and extends across said liner through said void, and between said thumb portion and said finger portion, and thence is adapted to extend around the back of the patient's hand adjacent the patient's knuckles.

6. The device of claim 1 wherein a plurality of separate spaced securement patches are secured to said first side of said splint to detachably cling to the material of said liner.

7. The resting hand orthosis of claim 1 wherein said finger portion is elongated so as to provide support for said fingers and each knuckle thereof.

8. The resting hand orthosis of claim 1 wherein said thumb portion has an arcuate shape and extends downwardly from said palm portion and rearwardly with respect to said finger portion so as to prevent both longitudinal and transverse adduction of the patient's thumb with respect to the patient's index finger.

* * * * *